United States Patent
Schätzl

(10) Patent No.: US 8,104,471 B2
(45) Date of Patent: Jan. 31, 2012

(54) APPARATUS AND METHOD FOR SURVEYING FLOW SIGNALS

(75) Inventor: Stefan Schätzl, Weilheim (DE)

(73) Assignee: Map Medizin-Technologie GmbH, Martinsried (DE)

( * ) Notice: Subject to any disclaimer, the term of this patent is extended or adjusted under 35 U.S.C. 154(b) by 1131 days.

(21) Appl. No.: 11/791,214

(22) PCT Filed: Nov. 24, 2005

(86) PCT No.: PCT/EP2005/012578
§ 371 (c)(1),
(2), (4) Date: Aug. 27, 2007

(87) PCT Pub. No.: WO2006/056445
PCT Pub. Date: Jun. 1, 2006

(65) Prior Publication Data
US 2008/0029097 A1    Feb. 7, 2008

(30) Foreign Application Priority Data
Nov. 24, 2004   (DE) .................... 10 2004 056 747

(51) Int. Cl.
*A61M 11/00*   (2006.01)
(52) U.S. Cl. .......... 128/204.21; 128/204.18; 128/204.23
(58) Field of Classification Search ............. 128/204.18, 128/204.21, 204.23, 204.26, 200.24, 200.26, 128/204.29, 203.12, 204.22
See application file for complete search history.

(56) References Cited

U.S. PATENT DOCUMENTS

| | | | |
|---|---|---|---|
| 5,845,636 A | 12/1998 | Gruenke et al. | |
| 6,142,952 A | 11/2000 | Behbehani et al. | |
| 7,086,399 B2* | 8/2006 | Makinson et al. | 128/204.21 |
| 7,882,834 B2* | 2/2011 | Gradon et al. | 128/204.23 |
| 2003/0066529 A1 | 4/2003 | Truschel et al. | |
| 2004/0123866 A1 | 7/2004 | Berthon-Jones | |

OTHER PUBLICATIONS

International Search Report for PCT/EP2005/056445 mailed Mar. 1, 2006 (English).

* cited by examiner

*Primary Examiner* — Steven Douglas
(74) *Attorney, Agent, or Firm* — Nixon & Vanderhye P.C.

(57) ABSTRACT

The invention is directed to an apparatus and a method for surveying and analyzing flow signals that can be picked up by means of flow measuring arrangements in the flow through breathing gas supply systems, in particular CPAP devices, air humidifiers, breathing gas lines, and breathing masks. One aspect of the invention is to furnish ways to increase the reliability of flow signals. In one embodiment, there is provided a device for evaluating a flow signal, picked up from a line provided for carrying breathing gas, having an electronic measurement data processor. The measurement data processor is configured such that it subjects the measurement data detected to a time-frequency-amplitude (TFA) series analysis and generates recordings, by which for the flow signal, the amplitude value of the frequencies contained is apparent.

19 Claims, 2 Drawing Sheets

APPARATUS AND METHOD FOR SURVEYING FLOW SIGNALS

CROSS-REFERENCE TO RELATED APPLICATION

This application is the US national phase of international application PCT/EP2005/012578 filed 24 Nov. 2005, which designated the U.S. and claims priority to DE 10 2004 056 747.6 filed 24 Nov. 2004, the entire contents of each of which are hereby incorporated herein by reference.

BACKGROUND OF THE INVENTION

The invention is directed to an apparatus and a method for surveying and analyzing flow signals that can be picked up by means of flow measuring arrangements in the flow through breathing gas supply systems, in particular CPAP devices, air humidifiers, breathing gas lines, and breathing masks.

For treating sleep-related breathing problems, it is known for a person who is to be treated to be supplied with a breathable gas, especially ambient air, at a pressure level that is above the ambient pressure level. The delivery of the breathing gas is typically done using an rpm-controlled blower. By delivering the breathing gas at a pressure level that is above the ambient pressure, it becomes possible to bring about a so-called pneumatic tracking effect in the upper airway region of the person to be treated, as a result of which obstructions in this airway region can be effectively prevented. The devices provided for pumping the breathing gas, in particular the ambient air, up to the elevated pressure level required for achieving the pneumatic tracking effect typically include a basic unit, in which a blower, intended for pumping the breathing gas, the electronics needed for triggering the blower, and typically also an air humidifier are provided. Carrying the breathing gas pumped through this basic unit to the patient to be treated is done via flexible tubing and a patient interface, e.g., a breathing mask, applied to the patient and coupled to the flexible tubing.

Typically, the basic units provided for pumping the breathing gas are designed such that they survey measurement signals indicative at least of the breathing gas flow and take them into account in regulating the pumping power of the blower.

Particularly, in relatively sensitive online or offline evaluation of the measurement signals surveyed by the flow sensors provided in the unit, it is possible that in the unit, the instantaneous physiological status of the patient is assessed imprecisely or inaccurately, and the breathing gas pressure ascertained on the basis of this imprecise or inaccurate assessment fails to take adequate account of the physiological needs of the patient.

SUMMARY

One aspect of the invention is to furnish ways to increase the reliability of flow signals.

According to one embodiment of the invention, there is provided an apparatus for evaluating a flow signal obtained from a gas delivery tube or line, the apparatus comprising an electronic measurement data processor, wherein the measurement data processor is configured such that it subjects the measurement data detected to a time-frequency-amplitude series analysis and generates recordings, by which, for the flow signal, the amplitude value of the frequencies is apparent.

According to another embodiment of the invention, there is provided a flow signal obtained from a gas delivery tube or line, the method comprising providing an electronic measurement data processor; subjecting the detected measurement data to a time-frequency-amplitude (TFA) analysis; generating recordings by which, for the flow signal, the amplitude value of the frequencies is apparent; and evaluating the flow signal in light of the TFA analysis.

According to another embodiment of the invention, there is provided a diagnostic apparatus for evaluating a gas flow signal comprising a flow sensor to produce flow signal measurement data; and a processor to process the measurement data to distinguish signal factors due to equipment from signal factors of physiological origin.

As a result, it advantageously becomes possible to subject the flow signal to a time-frequency analysis and to make an assessment of the flow signal that is more reliable and/or conclusive. It particular, it becomes possible to distinguish signal factors caused by the equipment from signal factors that are of physiological origin.

Further, it becomes possible to recognize artifacts in the flow signal and their origin. It moreover becomes possible to examine and assess the flow signals online as needed. The TFA analysis used on the flow signals can also be used in polysomnography systems or in display systems for therapeutic equipment.

It also becomes possible to examine accessories, such as masks, rinsing adapters, or hoses for artifacts that may be caused by these accessories, for instance so that precautionary measures in terms of regulating them can be taken when these accessories are used in self-adapting breathing gas delivery systems, because hardware-specific disturbances or extraneous factors in the flow signal can be recognized and compensated for.

It furthermore becomes possible to recognize artifacts in the flow signal that are caused by anatomical peculiarities, other body functions, or physiological problems of the person to be treated. By subjecting flow signals to a time-frequency-amplitude series analysis, it also becomes possible to implement more-extensive algorithms, taking these results of evaluation into account, for automatically adapting the pressure of a breathing gas supply unit. The TFA analysis can itself form a component of an algorithm for automatic diagnosis of breathing problems and/or for controlling pressure.

BRIEF DESCRIPTION OF THE DRAWINGS

Further details and characteristics are described below or will become apparent from the ensuing description in conjunction with the drawings, in which.

DETAILED DESCRIPTION OF PREFERRED EMBODIMENTS

By observing flow curves, which are preferably recorded by a substantially linear measurement system with low air resistance, conclusions can be drawn about the status of the airways of a patient. In employing this method in the sleep laboratory or in therapeutic equipment, the information contained in the signals picked up is often not interpreted, or possibly only incorrectly interpreted. By evaluating these flow signals using a TFA analysis, it becomes possible to recognize which factors and peripheral conditions can be ascribed to specific characteristics that can be found in the measurement signals.

In contrast to a purely time-related observation of the flow signal, TFA analysis can be used to determine whether a characteristic (such as low-frequency components of oscillation) originate in respiratory events, disturbances caused by turbulence in the mask, snoring, cardiogenic fluctuations in air pressure, and/or flow noises in the sensor itself. Using TFA analysis, the frequency of the oscillations can be examined more thoroughly. It can also be determined from the flow signal what proportion of the overall amplitude of the signal is made up of these various disturbances. Based on TFA analysis, it becomes possible for characteristics that are defined by certain frequency components to be replicated, recognized (on a repeated basis or at a later time) and compensated for as needed.

Using TFA analysis, it becomes possible to maintain a chronological association of the characteristics with their incidence in the flow curve. As a result, it can be determined whether a certain frequency component occurs at the end of an expiration phase, for instance, or at some other time. A method is thus created which makes it possible to observe the amplitudes of the frequency series analysis over time in the flow curve and thus to associate them with the flow curve as such. As a result, it is furthermore possible at any time in the flow curve to detect and assess the frequencies that occur in the flow curve.

Figure 1:
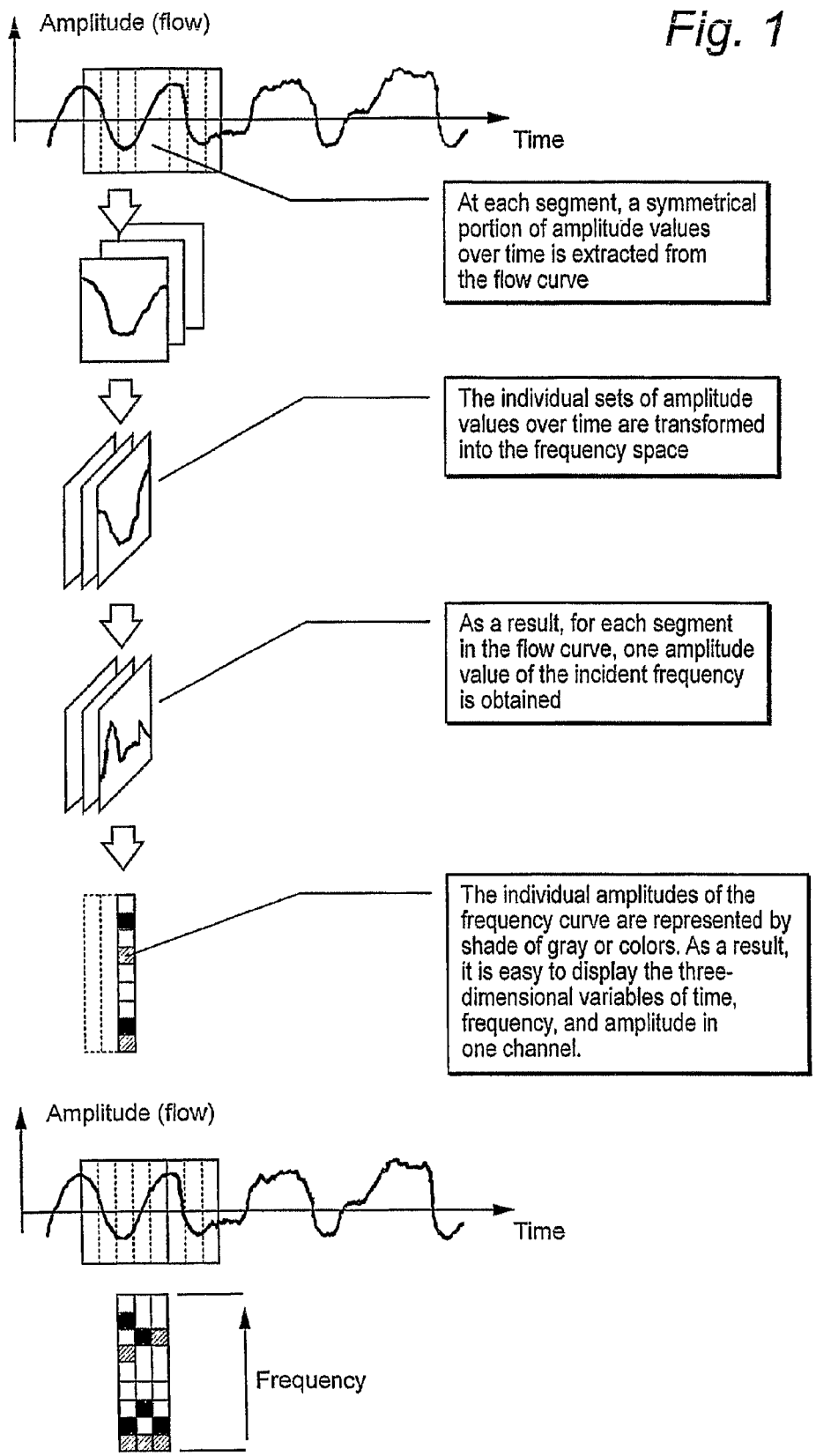
FIG. 1 illustrates a three-dimensional time-frequency-amplitude series analysis (TFA analysis) according to an embodiment of the present invention.

As FIG. 1 shows, in certain time segments Delta T (typically shorter than 0.5 seconds), symmetrical data portions are extracted from the flow signal at time TI.

The portions having the amplitude values are transformed to the frequency range by a suitable method (FFT, bandpass filters, RMS assessment). Because of the association with time TI of each data set, the chronological association of the frequency-transformed data is preserved.

The data in the frequency space are preferably then transformed to a linear or logarithmic scale, and the amplitude values are displayed by means of shades of gray or colors.

By means of this display principle, a display of the frequency spectrum is obtained for each time TI. If these individual displays are plotted in succession in the correct chronological association below the original flow curve, a quasi-three-dimensional display of the amplitudes of the frequencies over time, with the correct, unambiguous association with the flow curve, is obtained.

Figure 2:
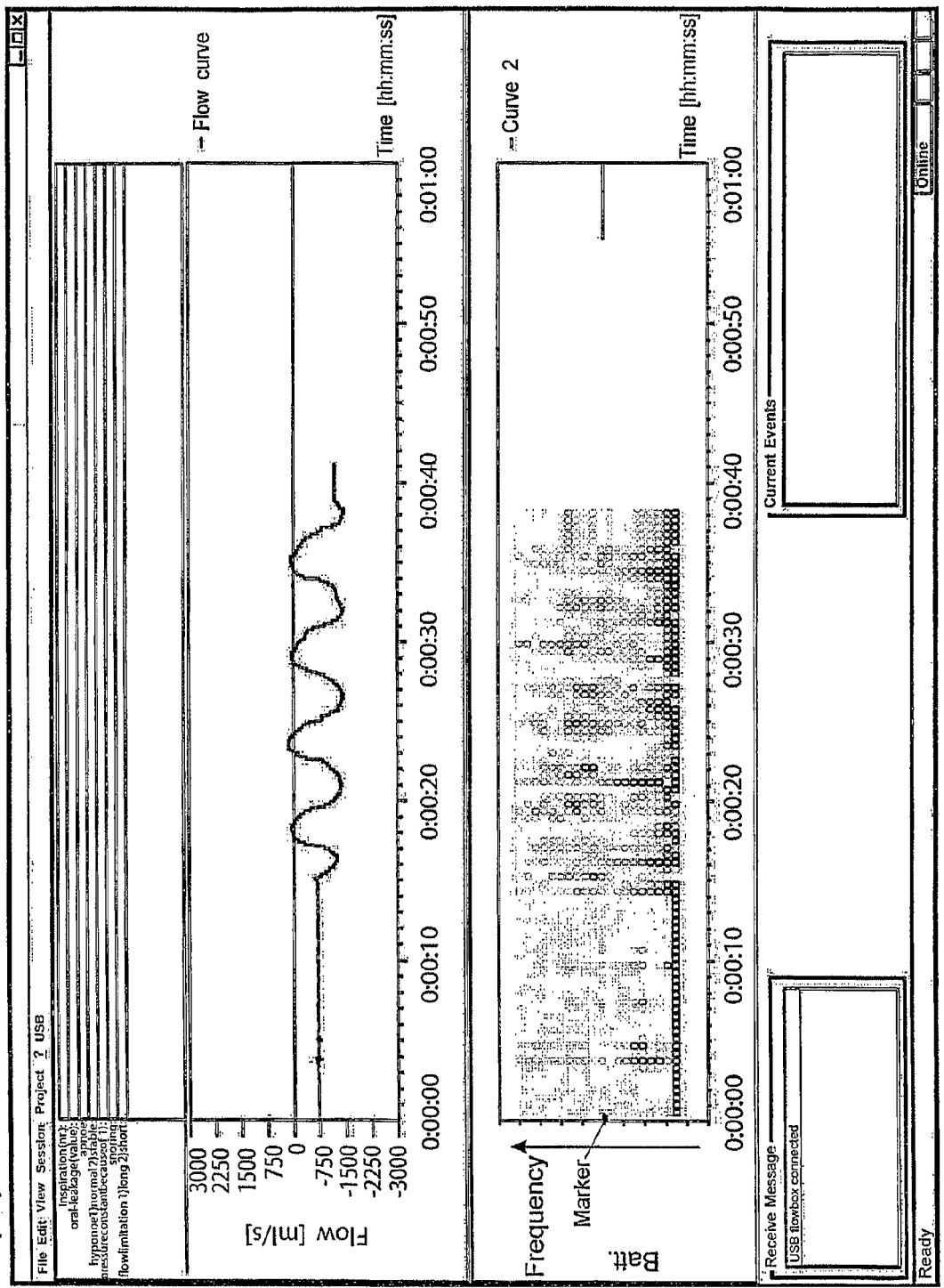
FIG. 2 is a screen shot showing the recordings generated according to an embodiment of the invention.

FIG. 2 is a screen shot showing one example of displaying the results of evaluation, surveyed in accordance with an embodiment of the invention, using a suitable viewer or monitor.

According to the above teachings, it becomes possible in particular to obtain the association with the original time signal. The occurrence of a certain frequency component, for instance, can also be associated precisely with a certain instant during expiration. It can thus be ascertained, for instance, whether a certain mask is snoring on exhalation, or whether characteristics in the final expiratory plateau are cardiac frequencies.

The flow signal can be picked up, e.g., as a differential pressure signal at a measurement diaphragm, ram pressure, or some other kind of flow resistance measurement point.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A method for evaluating a flow of breathable gas delivered to a patient through a gas delivery conduit or line, the method comprising:
   monitoring the flow of breathable gas that is delivered to a patient to obtain a flow signal;
   processing, via an electronic measurement data processor, the flow signal to obtain flow measurement data;
   dividing the flow measurement data into a plurality of segments, each one of the plurality of segments having at least some associated flow measurement data and also being associated with a time value along the flow signal;
   transforming the flow measurement data from each one of the plurality of segments into a frequency domain to obtain a plurality of frequencies per each one of the plurality of segments, each one of the plurality of frequencies having an associated frequency amplitude;
   associating the plurality of frequencies to the time value of the associated flow measurement data of the respective segment;
   storing the plurality of frequencies, the associated frequency amplitudes, and the time value for each one of the plurality of segments; and
   performing a process based on the association of at least one of the plurality of frequencies to the respective segment of the flow signal.

2. The method of claim 1, wherein the time value is over a time span of at least a portion of the flow signal.

3. The method of claim 2, wherein the time span has a length of less than about ½ a second.

4. The method of claim 1, wherein the process includes controlling a blower that provides the breathable gas through the gas delivery conduit or line.

5. The method of claim 1, wherein the process includes displaying a graph of the transformed data including a visual display of the plurality of frequencies and their associated amplitudes over the time period.

6. The method of claim 5, wherein the graph is a first graph and the process further includes displaying a second graph that includes a visual display of the flow signal over a time period.

7. The method of claim 5, wherein the associated frequency amplitudes are displayed in different colors and/or shades depending upon the amplitude.

8. The method of claim 1, wherein the process includes determining that at least one of the plurality of frequencies is a cardiac frequency that is associated with a time value of the flow signal.

9. A CPAP apparatus comprising:
   a blower that is configured to provide a flow of breathable gas to a patient; and
   at least one processor that is configured to receive a flow signal from a flow sensor that, in use, monitors the flow of breathable gas being delivered to the patient, the at least one processor being further configured to:

divide the flow signal into a plurality of data segments, each one of the plurality of data segments having flow measurement data, each one of the plurality of data segments associated with a time value within of the flow signal;

transform the flow measurement data from each one of the plurality of data segments into a frequency domain to obtain a plurality of frequencies per each one of the plurality of data segments, each one of the plurality of frequencies having an associated frequency amplitude;

associate the plurality of frequencies to the time value within the flow signal of the respective segment;

store the plurality of frequencies, the associated frequency amplitudes, and the time value associated with each one of the plurality of data segments; and perform a process based on the association of at least one of the plurality of frequencies to the respective segment of the flow measurement data.

10. The CPAP apparatus of claim 9, wherein the processor is further configured to compare the plurality of frequencies and associated frequency amplitudes to at least one stored predetermined frequency characteristic, and when the at least one stored predetermined frequency characteristic is determined to exist, store the frequency, predetermined frequency characteristic, and the time value of the flow signal that is associated with the determined respective frequency.

11. The CPAP apparatus of claim 9, wherein the at least one stored predetermined frequency includes a frequency that is associated with a humidifier, breathing gas line, breathing mask and/or, a rinsing adapter.

12. The CPAP apparatus of claim 9, wherein the processor is further configured to control the blower based on the association.

13. The CPAP apparatus of claim 9, further comprising a display,
wherein the at least one processor is further configured to output a graph o the display, the graph including a visual display of the plurality of frequencies and their associated amplitudes over the time period.

14. The CPAP apparatus of claim 13, wherein the graph is a first graph and the at least one processor is further configured to output a second graph to the display that includes a visual display of the flow signal over a time period, the second graph displayed in conjunction with the first graph on the display.

15. The CPAP apparatus of claim 13, wherein the associated amplitudes included in the second graph are to be displayed in different colors and/or shades depending on amplitude.

16. The CPAP apparatus of claim 9, wherein each one of the data segments is associated with a time span of less than about ½ a second.

17. The CPAP apparatus of claim 9, wherein the processor is further configured to determine that the at least one of the plurality of frequencies is a cardiac frequency that is associated with one of the time values within the flow signal.

18. The CPAP apparatus of claim 9, wherein the at least one processor is further configured to perform a fast Fourier transform to transform the flow measurement data into the frequency domain.

19. A non-transitory computer readable storage medium storing computer readable instructions for use evaluating a flow of breathable gas that is delivered to a patient via a blower, the stored instructions comprising instructions configured to:

monitor the flow of breathable gas that is delivered to a patient to obtain a flow signal;

process the flow signal to obtain flow measurement data;

divide the flow measurement data into a plurality of segments, each one of the plurality of segments having at least some associated flow measurement data and also being associated with a time value along the flow signal;

transform the flow measurement data from each one of the plurality of segments into a frequency domain to obtain a plurality of frequencies per each one of the plurality of segments, each one of the plurality of frequencies having an associated frequency amplitude;

associate the plurality of frequencies to the time value of the associated flow measurement data of the respective segment;

store the plurality of frequencies, the associated frequency amplitudes, and the time value for each one of the plurality of segments into a memory medium; and perform a process based on the association of at least one of the plurality of frequencies to the respective segment of the flow signal.

\* \* \* \* \*